(12) United States Patent
Li et al.

(10) Patent No.: US 10,955,497 B2
(45) Date of Patent: Mar. 23, 2021

(54) PHASE COMPENSATION CIRCUIT, MAGNETIC INDUCTION IMAGING DEVICE AND PHASE COMPENSATION METHOD

(71) Applicants: Beijing BOE Optoelectronics Technology Co., Ltd., Beijing (CN); BOE TECHNOLOGY GROUP CO., LTD., Beijing (CN)

(72) Inventors: Wei Li, Beijing (CN); Lei Xu, Beijing (CN); Meng Shi, Beijing (CN)

(73) Assignees: Beijing BOE Optoelectronics Technology Co., Ltd., Beijing (CN); BOE TECHNOLOGY GROUP CO., LTD., Beijing (CN)

( * ) Notice: Subject to any disclaimer, the term of this patent is extended or adjusted under 35 U.S.C. 154(b) by 41 days.

(21) Appl. No.: 16/408,211

(22) Filed: May 9, 2019

(65) Prior Publication Data
US 2020/0049778 A1  Feb. 13, 2020

(30) Foreign Application Priority Data
Aug. 10, 2018  (CN) .......................... 201810910401.9

(51) Int. Cl.
| | |
|---|---|
| G01R 33/31 | (2006.01) |
| A61B 5/05 | (2021.01) |
| G01R 33/389 | (2006.01) |
| H03L 7/24 | (2006.01) |
| A61B 5/0522 | (2021.01) |

(52) U.S. Cl.
CPC ............ *G01R 33/31* (2013.01); *A61B 5/0522* (2013.01); *G01R 33/389* (2013.01); *H03L 7/24* (2013.01)

(58) Field of Classification Search
CPC .... G01R 33/31; G01R 33/386; A61B 5/0522; H03L 7/24
See application file for complete search history.

(56) References Cited

U.S. PATENT DOCUMENTS

| | | | | |
|---|---|---|---|---|
| 2005/0035762 A1* | 2/2005 | Albrecht | ............ | G01R 33/3614 324/307 |
| 2015/0238114 A1* | 8/2015 | Feldkamp | ............ | A61B 5/7425 600/425 |
| 2017/0261357 A1* | 9/2017 | Wang | ........................ | G01F 1/74 |

\* cited by examiner

*Primary Examiner* — Gregory H Curran
(74) *Attorney, Agent, or Firm* — Thomas | Horstemeyer, LLP

(57) ABSTRACT

A phase compensation circuit includes a phase difference voltage detection module configured to process an inputted detection signal and an inputted reference signal, calculate a magnitude ratio or a phase difference of the processed detection signal and reference signal, and then output a first phase difference voltage signal according to the amplitude ratio or the phase difference. A compensation voltage adjustment module is configured to collect an ambient temperature parameter, determine a first compensation voltage corresponding to the ambient temperature parameter according to a corresponding relationship between a preset temperature parameter and a compensation voltage, perform voltage division on a voltage value inputted from a voltage input terminal according to the first compensation voltage, and output a compensation voltage signal; and a A compensation module is configured to compensate for the first phase difference voltage signal according to the compensation voltage signal and output a second phase difference voltage signal.

20 Claims, 3 Drawing Sheets

PHASE COMPENSATION CIRCUIT, MAGNETIC INDUCTION IMAGING DEVICE AND PHASE COMPENSATION METHOD

CROSS-REFERENCE TO RELATED APPLICATIONS

The present application claims the benefit of and priority to Chinese Patent Application No. 201810910401.9 filed Aug. 10, 2018, the entire contents of which are incorporated herein by reference.

TECHNICAL FIELD

The present disclosure relates to the field of medical detection technologies and, more particularly, to a phase compensation circuit, a magnetic induction imaging device, and a phase compensation method.

BACKGROUND

As a non-contact electronic medical device, a magnetic induction imaging device is mainly used for the detection of brain function, especially for functional imaging of cerebral edema and cerebral hemorrhage, or the like, which is mainly based on a principle of measurement of an eddy current signal: an excitation coil is inputted to an alternating current to generate an alternating magnetic field, a conductor to be tested is placed in the alternating magnetic field, and a magnetic flux passing through the conductor to be tested is changed. The conductor to be tested is regarded as a closed loop circuit, therefore, an induced current, i.e., eddy current, is generated inside the conductor and the greater the frequency of an excitation current, the greater the intensity of the eddy current. Meanwhile, a magnitude and distribution of the eddy current also reflect magnitude and distribution of an electrical conductivity of the conductor to be tested. The eddy current will further excite a secondary magnetic field, a direction of which may be judged by the right-handed screw rule, and the secondary magnetic field is superimposed with the original excitation magnetic field, thus information of the electrical conductivity of the conductor to be tested can be obtained by detecting information of the superimposed magnetic field. Intensity and distribution of the superimposed magnetic field are varied, when the intensity and distribution of the eddy current inside the conductor are changed as the magnitude and distribution of the electrical conductivity of the conductor to be tested are changed. An inverse problem of an electromagnetic field may be solved by sequentially changing a position of the excitation coil and using detection coils at different positions in space to detect a series of changes in induced current or induced voltage caused by a change in the superimposed magnetic field, and the conductor to be tested is imaged.

Based on a basic principle of electromagnetic induction tomography, a change in a phase difference between a detection signal and a reference signal before and after the placing of the conductor to be tested reflects the information of the electrical conductivity of the conductor to be tested. Meanwhile, a change in an amplitude of the detection signal can also reflect permeability and a dielectric constant of the conductor to be tested, but the change in the amplitude is extremely small and is more difficult to be measured than the phase difference, so the detection of the phase difference is emphasized. In a magnetic induction tomography system, high requirements are placed on the stability of a measurement system and the accuracy of phase measurements as the accuracy and stability of the phase measurements directly affect an imaging quality and a measurement result.

However, during the operation of the magnetic induction imaging device, heat will be generated which causes a change in temperature of an environment where the magnetic induction imaging device is placed, and there will be an additional phase difference in a detection system, which further leads to a lower accuracy of the measurement result.

It is to be noted that the above information disclosed in this Background section is only for enhancement of understanding of the background of the present disclosure and therefore it may contain information that does not form the prior art that is already known to a person of ordinary skill in the art.

SUMMARY

The present disclosure discloses a phase compensation circuit, including: a phase difference voltage detection module, a compensation voltage adjustment module, and a compensation module, wherein the phase difference voltage detection module is respectively connected to a detection signal input terminal, a reference signal input terminal and a phase difference voltage output terminal, which is coupled to the compensation module, and the phase difference voltage detection module is configured to process an inputted detection signal and an inputted reference signal, and calculate a magnitude ratio or a phase difference of the processed detection signal and reference signal, and output a first phase difference voltage signal according to the amplitude ratio or the phase difference; the compensation voltage adjustment module is respectively connected to a voltage input terminal and a compensation voltage output terminal, which is coupled to the compensation module, and the compensation voltage adjustment module is configured to collect an ambient temperature parameter, determine a first compensation voltage corresponding to the ambient temperature parameter according to a corresponding relationship between a preset temperature parameter and a compensation voltage, perform a voltage division on a voltage value according to the first compensation voltage, and output a compensation voltage signal; and the compensation module is configured to compensate for the first phase difference voltage signal according to the compensation voltage signal, and output a second phase difference voltage signal.

In an exemplary embodiment, the phase difference voltage detection module includes a differential amplifier circuit, a first buffer circuit, a second buffer circuit, a phase detecting circuit, and a filter circuit; wherein the differential amplifier circuit has a terminal, which is coupled to the detection signal input terminal, and another terminal, which is coupled to a receiving terminal of the first buffer circuit, and the differential amplifier circuit is configured to perform differential amplification on the detection signal, and output the detection signal on which the differential amplification is performed; the first buffer circuit has an output terminal which is coupled to a receiving terminal of the phase detecting circuit, and the first buffer circuit is configured to amplify the detection signal subjected to the differential amplification at a specified ratio, and output the amplified detection signal; the second buffer circuit has a receiving terminal which is connected to the reference signal input terminal, and an output terminal which is coupled to the receiving terminal of the phase detecting circuit, and the second buffer circuit is configured to amplify the reference signal at the specified ratio, and output the amplified reference signal; the phase detecting circuit also has an output terminal which is coupled to a receiving terminal of the filter circuit, and the phase detecting circuit is configured to calculate the amplitude ratio or the phase difference, convert the amplitude ratio or the phase difference into a phase difference voltage signal to be outputted; and the filter circuit has an output terminal which is coupled to a receiving terminal of the compensation module, and the filter circuit is configured to filter the phase difference voltage signal to obtain the first phase difference voltage signal to be outputted.

In an exemplary embodiment, the phase detecting circuit is an AD8302 analog phase detecting chip.

In an exemplary embodiment, the filter circuit is an active low pass filter.

In an exemplary embodiment, the compensation voltage adjustment module includes a temperature acquisition module, a micro control unit, a programmable resistor network, and a voltage divider network; wherein the temperature acquisition module is configured to collect the ambient temperature parameter; the micro control unit is coupled to the temperature acquisition module, the voltage input terminal, and the programmable resistor network, respectively, and the micro control unit is configured to receive the ambient temperature parameter and the voltage value, and compare the ambient temperature parameter with a specified temperature threshold parameter, and then output a control signal and the voltage value according to the comparion result; an output terminal of the programmable resistor network is coupled to the voltage divider network, and the programmable resistor network is configured to perform voltage division on the voltage value according to the control signal to obtain a first voltage value, and output the first voltage value; and an output terminal of the voltage divider network is connected to the compensation module, and the voltage divider network is configured to perform secondary voltage division on the first voltage value to generate a second voltage value, and convert the second voltage value into a compensation voltage signal, and then output the compensation voltage signal.

In an exemplary embodiment, the temperature acquisition module is a temperature sensor.

In an exemplary embodiment, the micro control unit is a single chip AT89S52.

In an exemplary embodiment, the voltage value is 5V.

In an exemplary embodiment, the compensation module includes a voltage amplifier, which is connected to the filter circuit and the voltage divider network, respectively, and the voltage amplifier is configured to amplify the first phase difference voltage signal and the second phase difference voltage signal at the same ratio.

The present disclosure also discloses a magnetic induction imaging device including the phase compensation circuit according to any of the above-described contents.

The present disclosure also discloses a phase compensation method, which is applied to the phase compensation circuit according to any of the above-described contents, the method includes: inputting a detection signal to a detection signal input terminal, a reference signal to a reference signal input terminal, and a voltage value to a voltage input terminal, respectively; determining a phase difference voltage signal based on an amplitude ratio of or a phase difference between the detection signal and the reference signal; collecting an ambient temperature parameter; determining a first compensation voltage corresponding to the ambient temperature parameter according to a correspondence relationship between a preset temperature parameter and a compensation voltage; performing voltage division on the voltage value according to the first compensation voltage, to output a compensation voltage signal; and performing phase compensation on the phase difference voltage signal according to the compensation voltage signal.

DETAILED DESCRIPTION

In order to make the above objectives, features, and advantages of the present disclosure more apparent, the present disclosure will be further described in detail with reference to the accompanying drawings and specific embodiments.

Figure 1:
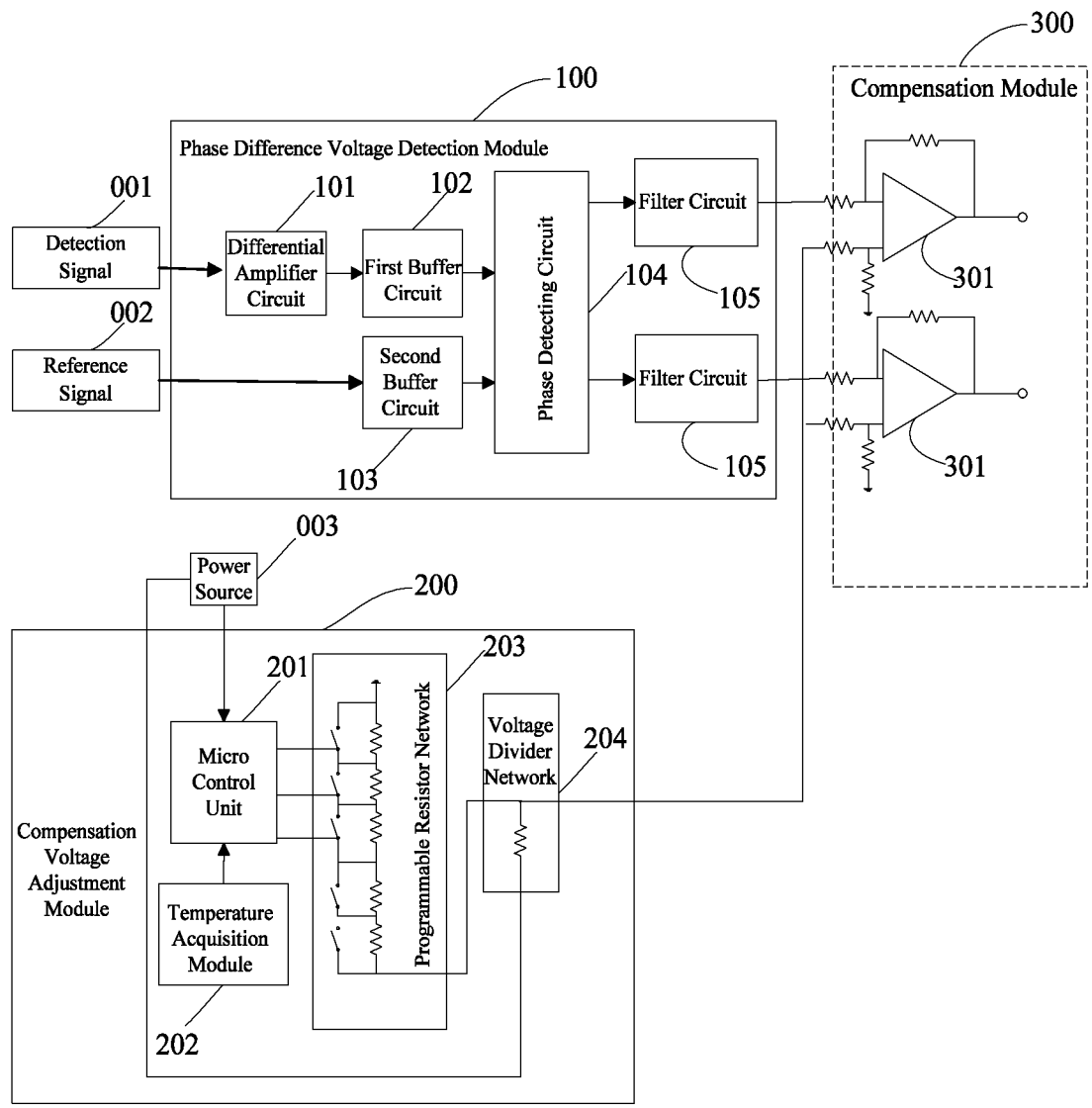
FIG. 1 is a block diagram illustrating a phase compensation circuit according to an embodiment of the present disclosure.

FIG. 1 is a block diagram illustrating a phase compensation circuit according to an embodiment of the present disclosure. The phase compensation circuit may include a phase difference voltage detection module 100, a compensation voltage adjustment module 200, and a compensation module 300.

The phase difference voltage detection module 100 is respectively connected to a detection signal input terminal 001, a reference signal input terminal 002, and a phase difference voltage output terminal (not shown). The phase difference voltage output terminal is coupled to the compensation module 300. The phase difference voltage detection module 100 is configured to process inputted detection signal and reference signal, and calculate an amplitude ratio or a phase difference of the processed detection signal and reference signal, and then output a first phase difference voltage signal according to the amplitude ratio or the phase difference.

The compensation voltage adjustment module 200 is respectively connected to a voltage input terminal 003 and a compensation voltage output terminal (not shown), which is coupled to the compensation module 300. The compensation voltage adjustment module 200 is configured to collect an ambient temperature parameter, determine a first compensation voltage corresponding to the ambient temperature parameter according to a corresponding relationship between a preset temperature parameter and a compensation voltage, divide voltage inputted by the voltage input terminal 003 according to the first compensation voltage, and output a compensation voltage signal.

The compensation module 300 is configured to compensate for the first phase difference voltage signal according to the compensation voltage signal, and output a second phase difference voltage signal.

The present disclosure may alleviate the problem of an additional phase difference in a system due to the ambient temperature parameter by measuring the ambient temperature parameter and performing phase compensation, which further ensures the accuracy of a measurement result and improves an imaging effect.

Next, the above-described phase difference voltage detection module 100 in the embodiments of the present disclosure will be described in detail with reference to the following exemplary embodiments.

In an exemplary embodiment of the present disclosure, the phase difference voltage detection module 100 may include a differential amplifier circuit 101, a first buffer circuit 102, a second buffer circuit 103, a phase detecting circuit 104, and a filter circuit 105 (as shown in FIG. 1).

As shown in FIG. 1, the differential amplifier circuit 101 has a terminal, which is coupled to the detection signal input terminal 001, and another terminal, which is coupled to the first buffer circuit 102, and the differential amplifier circuit may perform differential amplification on the inputted detection signal. The detection signal is preamplificated in the form of double-ended differential input before it is inputted to the phase detecting circuit 104, because, on one hand, it is not easy to obtain an accurate result if the detection signal, which may be only several tens of millivolts, is directly inputted to the phase detecting circuit 104, and one other hand, in the form of single-ended input, a ground terminal may introduce interference, and a current to ground is larger, thereby causing a larger signal loss. Compared with a conventional single-ended operational amplifier, the differential amplifier circuit 101 has a significantly high common mode rejection ratio, and if a signal generated by an electric field is regarded as a common mode signal, the use of differential input may reduce influence brought by the common mode signal and decrease a capacitive coupling of the system; meanwhile, the differential amplifier circuit 101 has a high input impedance, and includes positive and inverse phase terminals having equal input resistances, the differential amplifier circuit 101 therefore does not require high impedance matching, and is less sensitive to a feedback resistance and a gain resistance of a circuit, it also has a symmetrical dynamic response of +1 and −1 gain with constant power consumption and does not vary with a common mode voltage.

The first buffer circuit 102 has an output terminal which is coupled to a receiving terminal of the phase detecting circuit 104, and the first buffer circuit 102 may amplify the detection signal subjected to the differential amplification based on a specified ratio and output the amplified detection signal.

It is to be understood that the specified ratio may be obtained by the person skilled in the art through multiple tests according to actual requirements, and a specific value or a numerical range of the specified ratio is not limited by the embodiments of the present disclosure.

The second buffer circuit 103 has a receiving terminal which is connected to the reference signal input terminal 002, and an output terminal which is coupled to the receiving terminal of the phase detecting circuit 104, and the second buffer circuit 103 may amplify the inputted reference signal based on a specified ratio, and output the amplified reference signal.

It can be understood that this specified ratio corresponds to the specified ratio based on which the detection signal is amplified, alternatively, the two specified ratios are the same.

As a special amplifier circuit, the first buffer circuit 102 and the second buffer circuit 103 may employ an operational amplifier as its core, and are often used for isolation, impedance matching, and the enhancement of a circuit output capability. Unlike other voltage amplifiers or power amplifiers, the first buffer circuit 102 and the second buffer circuit 103 generally have an amplification factor of 1:1, although failing to amplify voltage or current for a signal, they perform the function of impedance matching and excellently reduce signal distortion, and also enhance an anti-interference capability of the circuit.

The phase detecting circuit 104 also has an output terminal which is coupled to a receiving terminal of the filter circuit 105, and the phase detecting circuit 104 may calculate an amplitude ratio or a phase difference of the amplified detection signal and reference signal, and convert the amplitude ratio or the phase difference to a phase difference voltage signal to be outputted.

The phase detecting circuit 104 converts the phase difference between the two input signals (i.e., the detection signal and the reference signal) into another output signal, which may be an analog voltage or a digital quantity. The phase detecting circuit 104 is an analog phase detecting circuit, when the output signal is an analog voltage, and the phase detecting circuit 104 is a digital phase detecting circuit, when the output signal is a digital quantity. In the system, one of the two input signals is the reference signal, and the other is the detection signal. In the present disclosure, by using an AD8302 analog phase detecting chip, the phase detecting circuit 104 may measure the amplitude ratio of and the phase difference between the two signals, and it is obtained through measurement that a frequency of the signals ranges from a low frequency to 2.7 GHz. The amplitude ratio has a measurement accuracy of 30 mV/Degree, and a measurement range of −30 dB to 30 dB, and the phase difference has a measurement accuracy of 10 mV/Degree, and a measurement range of 0° to 180°. In a low frequency band, when a single-ended +5V power source is used for power supply and an input resistance is 3 kΩ, in a system having an input impedance of 50Ω and an input range of −60 dBm to 0 dBm, a measured output voltage range of both the amplitude ratio and phase difference is 0V~1.8V.

A relationship between the phase difference and an output voltage measured based on the phase difference may be given in equation (1) as follows:

$$V_{out}(mV)=-10(\Delta\varphi-90°\ C.)+900 \tag{1}$$

Where $v_{out}$ represents the output voltage, and $\Delta\varphi$ represents the phase difference.

The amplitude ratio of the detection signal and the reference signal may be calculated with reference to a method for the calculation of an amplitude ratio commonly used in an existing technical solution, which will not be elaborated herein by the embodiments of the present disclosure.

It is to be understood that the examples above are provided merely for better understanding of technical solutions of the embodiments of the present disclosure, and are not intended to be the only implementation of the present disclosure.

The filter circuit 105 has an output terminal which is coupled to a receiving terminal of the compensation module 300, and the filter circuit 105 may filter the phase difference voltage signal outputted by the phase detecting circuit 104 to obtain a first phase difference voltage signal to be outputted.

In an embodiment of the present disclosure, the filter circuit 105 may be an active low-pass filter, which may filter out a noise in the phase difference voltage signal. The active low-pass filter employed in the present disclosure may have an extremely low cutoff frequency, and have no strict requirement for bandwidth, which greatly reduces the cost of a circuit design.

Next, the above-described compensation voltage adjustment module 200 in the embodiments of the present disclosure will be described in detail with reference to the following example embodiments.

Figure 2:
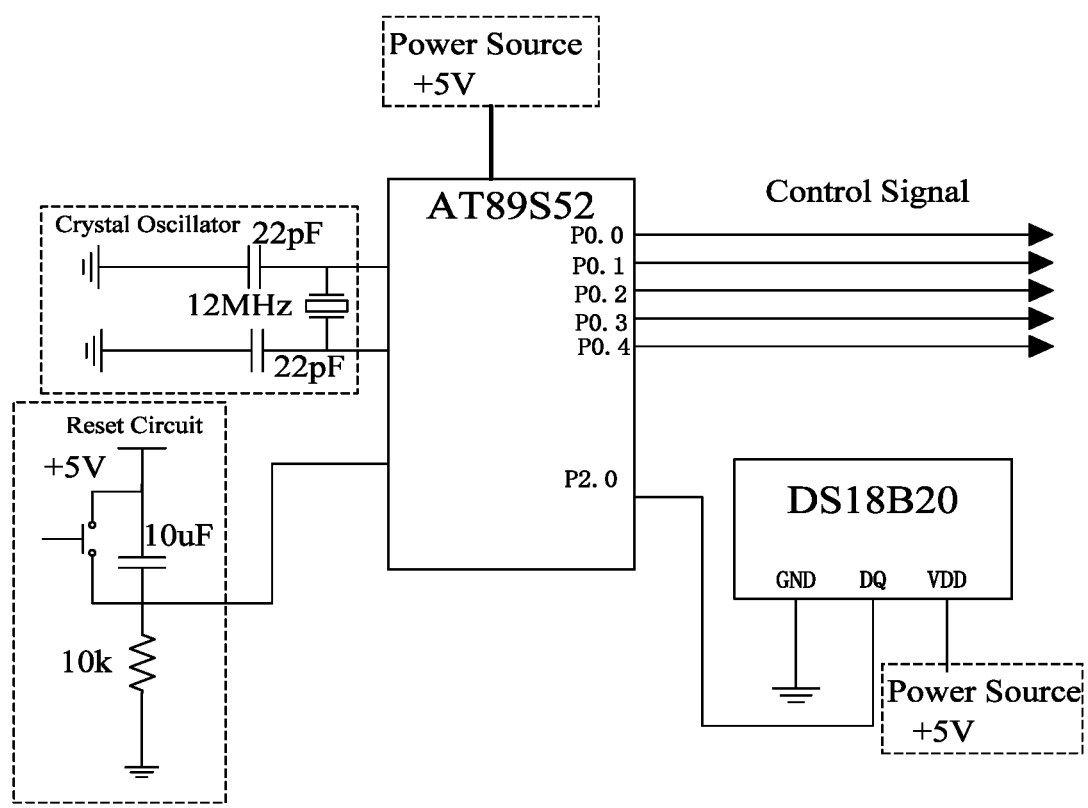
FIG. 2 is a block diagram illustrating a temperature acquisition circuit according to an embodiment of the present disclosure.

FIG. 2 is a block diagram illustrating a temperature acquisition circuit according to an embodiment of the present disclosure, which will be described below in conjunction with FIGS. 1 and 2.

In an exemplary embodiment of the present disclosure, the compensation voltage adjustment module 200 may include a temperature acquisition module 202, a micro control unit 201, a programmable resistor network 203, and a voltage divider network 204.

The temperature acquisition module 202 may be used to collect an ambient temperature parameter of an environment in which the system is located. The temperature acquisition module 202 may use a temperature sensor to transmit the collected temperature parameter through a DQ pin (as shown in FIG. 2). In an embodiment of the present disclosure, the temperature sensor is a DS18B20 temperature sensor.

The micro control unit 201 may be coupled to the temperature acquisition module 202, the voltage input terminal 003, and the programmable resistor network 203, respectively. The micro control unit 201 may receive the ambient temperature parameter transmitted from the temperature acquisition module 202, as well as a value of voltage inputted by the power source from the voltage input terminal 003, further compare the ambient temperature parameter with a specified temperature threshold parameter, and then output a control signal and the value of voltage according to the comparison result.

In an embodiment of the present disclosure, the Micro Control Unit 201 (MCU) may employ a single chip AT89S52, which may have a voltage value of +5V. As shown in FIG. 2, the micro control unit 201 may read an ambient temperature parameter collected by the DS18B20 temperature sensor via a general I/O interface P2.0, and convert it into a control signals of a programmable network to be outputted through a P0 group general-purpose I/O interface.

A procedure in which the DS18B20 temperature sensor reads the ambient temperature parameter may be shown with the following codes:

for(i=0;i<2;i++){
Temperature[i]=DS1820_ReadData( );//two 8-bit registers share ambient temperature parameters//Temperature[1] and Temperature[2]}

According to the operating principle of the DS18B20 temperature sensor, two 8-bit register values form 16-bit ambient temperature parameters, and the first 5 digits are sign bits which indicate positive and negative temperature values. If a positive temperature value is indicated, a measured value is multiplied by 0.0625 to obtain an actual temperature; and if a negative temperature is indicated, a measured value is inverted and added to 1 and then multiplied by 0.0625 to obtain an actual temperature. A working state of a phase detection system is optimal at a normal temperature (25° C.), which is thus used as a reference, and a relationship between a measured ambient temperature parameter and a control signal to be outputted may be calculated as follows, wherein a number of bits, an initial value, and a step of the control signal may be defined according to a desried accuracy, and making adjustament every 2 degrees will now be taken as an example.

The two known signals (i.e., the detection signal and the reference signal) with a phase difference of 90 degrees therebetween are inputted into the phase detection system, which is then heated, and the phase difference is measured, so a phase drift value corresponding to temperature rise may be obtained. Corresponding relationships between them are shown in Table 1 below:

TABLE 1

| Temperature | Phase Shift | Compensation Voltage | Control Signal |
|---|---|---|---|
| 25 | 0 | 0 | 00000 |
| 27 | 2 | 20 mv | 00001 |
| 29 | 4 | 40 mv | 00010 |
| 31 | 6 | 60 mv | 00100 |
| ... | ... | ... | |

In an embodiment of the present disclosure, the phase shift is a phase error.

Figure 3:
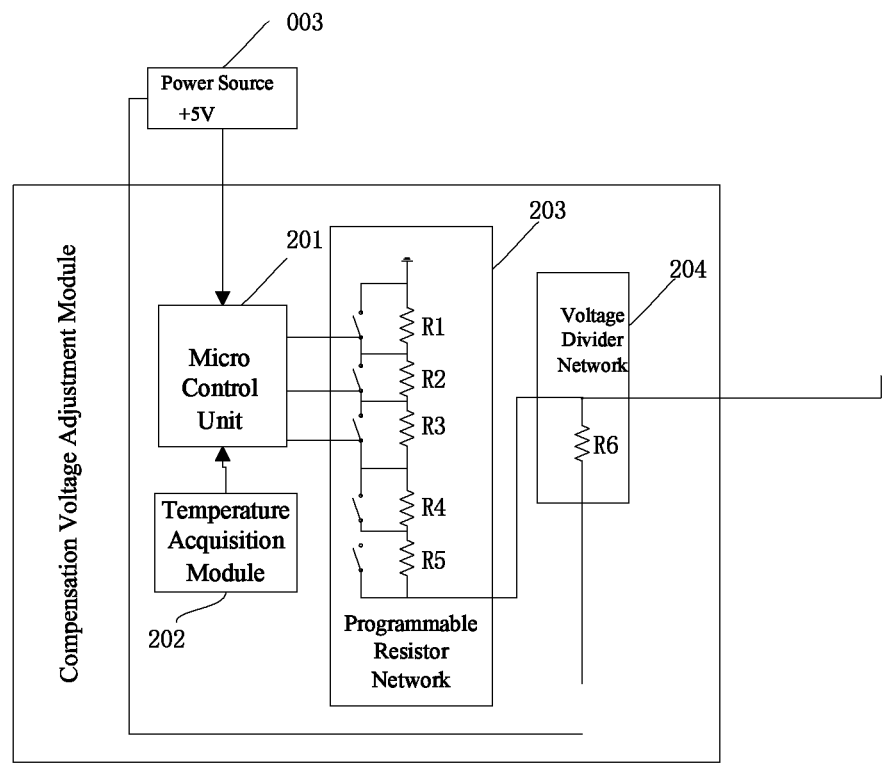
FIG. 3 is a block diagram illustrating a temperature compensation circuit according to an embodiment of the present disclosure.

FIG. 3 is a block diagram illustrating a temperature compensation circuit according to an embodiment of the present disclosure. As shown in FIG. 3, a voltage value inputted from a voltage input terminal 003 (i.e., a power source) is +5V, a programmable resistor network 203 is provided with five resistors R1, R2, R3, R4, and R5 in advance, which are configured to perform a voltage division process on the inputted voltage value, and a voltage divider network 204 is provided with a resistor R6 in advance. An output terminal of the programmable resistor network 203 may be coupled to the voltage divider network 204. The programmable resistor network 203 may receive the control signal outputted by the micro control unit 201, and divide the voltage value according to the control signal to obtain a first voltage value, and output the first voltage value. As shown in Table 1 above, a resistance value of the programmable network is: R1×bit0+R2×bit1+R3×bit2+R4×bit3+R5×bit4=R. The compensated voltage value is: 5V×R÷R6=compensation voltage; if corresponding relationships between the temperature rise and the phase shift are as shown in Table 1 above, R1=R2=R3=R4=R5=20Ω, R6=5KΩ. It can be satisfied that the control signal 00001: 20 Ω/5 KΩ×5 V=20 mV, and the control signal 00010: 40 Ω/5 KΩ×5 V=40 mV . . . .

It is to be understood that the examples above are provided merely for better understanding of technical solutions of the embodiments of the present disclosure, and are not intended to be the only limitation of the present disclosure.

An output terminal of the voltage divider network 204 is connected to a compensation module 300. The voltage divider network 204 may perform a secondary voltage dividing process on the first voltage value outputted by the programmable resistor network 203 to generate a second voltage value, and convert the second voltage value into a compensation voltage signal, and then output the compensation voltage signal.

Next, the compensation module 300 will be described below in detail with reference to the following exemplary embodiments.

The compensation module 300 may include a voltage amplifier 301, which may be connected to the filter circuit 105 and the voltage divider network 204, respectively. The voltage amplifier 301 may amplify the first phase difference voltage signal and the second phase difference voltage signal at the same ratio.

In the present disclosure, the voltage amplifier 301 may be a voltage amplifier or a power amplifier, etc., which is not limited in the embodiments of the present disclosure.

In the phase compensation circuit provided by the embodiment of the present disclosure, the phase difference voltage detection module processes the inputted detection signal and reference signal, and calculates the amplitude ratio of or the phase difference between the processed detection signal and reference signal, and then outputs the first phase difference voltage signal according to the amplitude ratio or the phase difference. The compensation voltage adjustment module collects the ambient temperature parameter, determines the first compensation voltage corresponding to the ambient temperature parameter according to the corresponding relationship between the preset temperature parameter and the compensation voltage, and divides voltage inputted by the voltage input terminal according to the first compensation voltage, and then outputs the compensation voltage signal; further, the compensation module compensates for the first phase difference voltage signal according to the compensation voltage signal, and outputs the second phase difference voltage signal. The embodiment of the present disclosure may alleviate the problem of an additional phase difference in a system due to the ambient temperature parameter by measuring the ambient temperature parameter and performing phase compensation, which further ensures the accuracy of a measurement result and improves an imaging effect.

Figure 4:
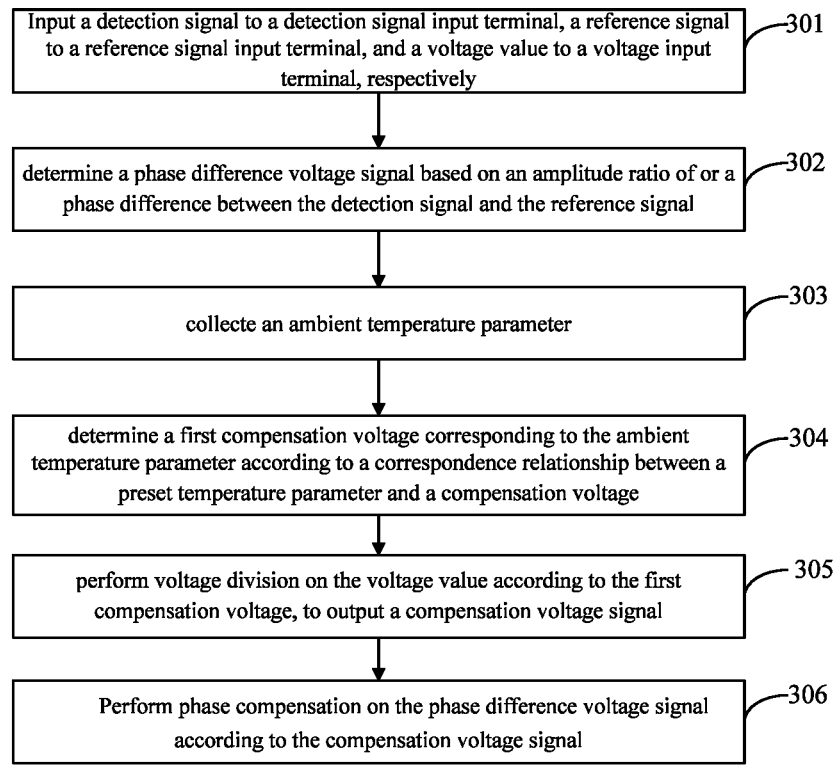
FIG. 4 is a flow chart showing steps of a phase compensation method according to an embodiment of the present disclosure.

FIG. 4 is a flow chart showing steps of a phase compensation method according to an embodiment of the present disclosure. The phase compensation method may include the following steps.

In step 301, a detection signal is inputted to a detection signal input terminal, a reference signal is inputted to a reference signal input terminal, and a voltage value is inputed to a voltage input terminal, respectively.

In the embodiment of the present disclosure, a phase compensation circuit may include a phase difference voltage detection module and a compensation voltage adjustment module. The phase difference voltage detection module may be connected to the detection signal input terminal and the reference signal input terminal to receive the detection signal and the reference signal. The compensation voltage adjustment module may be connected to the voltage input terminal to receive the voltage value inputted from the voltage input termianl.

Step 302 is performed when the detection signal, the reference signal, and the voltage value are received.

In the step 302, a phase difference voltage signal is determined based on an amplitude ratio of or a phase difference between the detection signal and the reference signal.

After the detection signal and the reference signal are acquired, an amplitude ratio or a phase difference of the detection signal and the reference signal may be calculated, and then a phase difference voltage signal is determined according to the amplitude ratio or the phase difference.

In an embodiment of the present disclosure, a phase detecting circuit is provided in the system in advance, which is configured to convert the amplitude ratio or the phase difference of the detection signal and the reference signal into a phase difference voltage signal.

Step 303 is carried out after the determining of the phase difference voltage signal.

In the step 303, an ambient temperature parameter is collected.

In the system, a temperature acquisition module such as a DS18B20 temperature sensor is provided in advance, which may be configured to monitor in real time ambient temperature parameter of an environment where the system resides.

In practical application, the person skilled in the art may obtain, in other ways, the ambient temperature parameter of the environment in which the system is located, which is not limited by the embodiments of the present disclosure.

Step 304 is performed after the ambient temperature parameter is collected.

In the step 304, a first compensation voltage corresponding to the ambient temperature parameter is determined according to a correspondence relationship between a preset temperature parameter and a compensation voltage.

In an embodiment of the present disclosure, the correspondences between the temperature parameter and the compensation voltage is preset, and the first compensation voltage corresponding to the ambient temperature parameter may be determined according to the correspondences.

Step 305 is performed after the first compensation voltage corresponding to the ambient temperature parameter is determined.

In the step 305, voltage division is performed on the voltage value according to the first compensation voltage to output a compensation voltage signal.

After the first compensation voltage corresponding to the ambient temperature parameter is determined, the voltage value inputted by the voltage input terminal may be subjected to voltage division according to the first compensation voltage, so that the voltage value on which the voltage division is performed is the same as a voltage value corresponding to the first compensation voltage.

After the voltage division is performed, the divided voltage value may be converted into a compensation voltage signal to be outputted, and then step 306 is performed.

In step 306, phase compensation is performed on the phase difference voltage signal according to the compensation voltage signal.

The phase difference voltage signal may be subjected to phase compensation according to the compensation voltage signal after the compensation voltage signal is obtained, so that the influence of changes in an ambient temperature on the system may be ignored.

In the phase compensation circuit provided by the embodiment of the present disclosure, the phase difference voltage detection module processes the inputted detection signal and reference signal, and calculates the amplitude ratio of or the phase difference between the processed detection signal and reference signal, and then outputs the first phase difference voltage signal according to the amplitude ratio or the phase difference. The compensation voltage adjustment module collects the ambient temperature parameter, determines the first compensation voltage corresponding to the ambient temperature parameter according to the corresponding relationship between the preset temperature parameter and the compensation voltage, and divides voltage inputted by the voltage input terminal according to the first compensation voltage, and then outputs the compensation voltage signal. Further, the compensation module compensates for the first phase difference voltage signal according to the compensation voltage signal, and outputs the second phase difference voltage signal. The embodiment of the present disclosure may alleviate the problem of an additional phase difference in a system due to the ambient temperature parameter by measuring the ambient temperature parameter and performing phase compensation, which further ensures the accuracy of a measurement result and improves an imaging effect.

Another embodiment of the present disclosure further discloses a magnetic induction imaging device, which may include the phase compensation circuit according to any of the first embodiment above-described.

Simply, the foregoing method embodiments are all expressed as a series of action combinations, but those skilled in the art should know that the present disclosure is not limited by the order of the actions described herein, it is because that according to the present disclosure, some steps can be performed in other orders or simultaneously. Secondly, those skilled in the art should also understand that the embodiments described in the description are all exemplary embodiments, and the involved actions and modules are not necessarily required by the present disclosure.

The embodiments in the description are described in a progressive manner, and each of the embodiments focuses on differences from other embodiments, and the same or similar parts among the embodiments can be referred to each other.

Finally, it should also be noted that, in this text, relational terms such as first and second, etc., are only used to distinguish one entity or operation from another entity or operation, and do not necessarily require or imply any such actual relations or orders present between these entities or operations. Moreover, the terms "including", "comprising" or any other variations thereof are intended to cover a non-exclusive inclusion such that processes, methods, articles, or devices that comprise a series of elements include not only those elements but also include other elements that are not explicitly listed. Alternatively, elements inherent to such processes, methods, articles, or devices may also be included. In case of no more limitations, an element defined by phase "including a . . ." does not exclude the situation where additional identical elements are present in the processes, the methods, the articles, or the devices including the element.

A phase compensation circuit, a magnetic induction imaging device, and a phase compensation method provided by the present disclosure are described above in detail. Specific examples are used herein to describe the principles and embodiments of the present disclosure. The description of the embodiments above is only intended to help the understanding of the method and its core idea of the present disclosure; meanwhile, those of ordinary skill in the art, according to the idea of the present disclosure, will make changes in the specific embodiments and application ranges. In summary, the contents of this description should not be constructed as limiting the present disclosure.

What is claimed is:

1. A phase compensation circuit, comprising:
   a phase difference voltage detection module, a compensation voltage adjustment module, and a compensation module;
   wherein the phase difference voltage detection module is connected to a detection signal input terminal, a reference signal input terminal, and a phase difference voltage output terminal, the phase difference voltage output terminal being coupled to the compensation module, and the phase difference voltage detection module being configured to process an inputted detection signal and an inputted reference signal, calculate a magnitude ratio of the processed detection signal and reference signal or a phase difference of the processed detection signal and reference signal, and then output a first phase difference voltage signal according to the amplitude ratio or the phase difference;
   wherein the compensation voltage adjustment module is connected to a voltage input terminal and a compensation voltage output terminal, the compensation voltage output terminal being coupled to the compensation module, and the compensation voltage adjustment module being configured to collect an ambient temperature parameter, determine a first compensation voltage corresponding to the ambient temperature parameter according to a corresponding relationship between a preset temperature parameter and a compensation voltage, perform voltage division on a voltage value inputted from the voltage input terminal according to the first compensation voltage, and output a compensation voltage signal; and
   wherein the compensation module is configured to compensate for the first phase difference voltage signal according to the compensation voltage signal and output a second phase difference voltage signal.

2. The phase compensation circuit according to claim 1, wherein the phase difference voltage detection module comprises a differential amplifier circuit, a first buffer circuit, a second buffer circuit, a phase detecting circuit, and a filter circuit;
   wherein the differential amplifier circuit has a terminal coupled to the detection signal input terminal and another terminal coupled to a receiving terminal of the first buffer circuit, and the differential amplifier circuit is configured to perform differential amplification on the detection signal, and output the detection signal on which the differential amplification is performed;
   the first buffer circuit has an output terminal which is coupled to a receiving terminal of the phase detecting circuit, and the first buffer circuit is configured to amplify the detection signal subjected to the differential amplification at a specified ratio, and output the amplified detection signal;
   the second buffer circuit has a receiving terminal connected to the reference signal input terminal and an output terminal coupled to the receiving terminal of the phase detecting circuit, and the second buffer circuit is configured to amplify the reference signal at the specified ratio, and output the amplified reference signal;
   the phase detecting circuit has an output terminal coupled to a receiving terminal of the filter circuit, and the phase detecting circuit is configured to calculate the amplitude ratio or the phase difference, convert the amplitude ratio or the phase difference into a phase difference voltage signal to be outputted; and
   the filter circuit has an output terminal coupled to a receiving terminal of the compensation module, and the filter circuit is configured to filter the phase difference voltage signal to obtain the first phase difference voltage signal to be outputted.

3. The phase compensation circuit according to claim 2, wherein the phase detecting circuit is an analog phase detecting chip.

4. The phase compensation circuit according to claim 2, wherein the filter circuit is an active low pass filter.

5. The phase compensation circuit according to claim 1, wherein:
   the compensation voltage adjustment module comprises a temperature acquisition module, a micro control unit, a programmable resistor network, and a voltage divider network;
   the temperature acquisition module is configured to collect the ambient temperature parameter;
   the micro control unit is coupled to the temperature acquisition module, the voltage input terminal, and the programmable resistor network, respectively, and the micro control unit is configured to receive the ambient temperature parameter and the voltage value inputted from the voltage input terminal, and compare the ambient temperature parameter with a specified temperature threshold parameter, and then output a control signal and the voltage value according to a result of the comparison;

an output terminal of the programmable resistor network is coupled to the voltage divider network, and the programmable resistor network is configured to perform voltage division on the voltage value according to the control signal to obtain a first voltage value and output the first voltage value; and an output terminal of the voltage divider network is connected to the compensation module, and the voltage divider network is configured to perform secondary voltage division on the first voltage value to generate a second voltage value, convert the second voltage value into a compensation voltage signal, and then output the compensation voltage signal.

6. The phase compensation circuit according to claim 5, wherein the temperature acquisition module is a temperature sensor.

7. The phase compensation circuit according to claim 5, wherein the micro control unit is a single chip.

8. The phase compensation circuit according to claim 5, wherein the voltage value is 5V.

9. The phase compensation circuit according to claim 5, wherein the compensation module comprises a voltage amplifier connected to the filter circuit and the voltage divider network, respectively, and the voltage amplifier is configured to amplify the first phase difference voltage signal and the second phase difference voltage signal at the same ratio.

10. A magnetic induction imaging device, comprising the phase compensation circuit according to claim 1.

11. The magnetic induction imaging device according to claim 10, wherein the phase difference voltage detection module comprises a differential amplifier circuit, a first buffer circuit, a second buffer circuit, a phase detecting circuit, and a filter circuit;

wherein the differential amplifier circuit has a terminal coupled to the detection signal input terminal and another terminal coupled to a receiving terminal of the first buffer circuit, and the differential amplifier circuit is configured to perform differential amplification on the detection signal, and output the detection signal on which the differential amplification is performed;

the first buffer circuit has an output terminal which is coupled to a receiving terminal of the phase detecting circuit, and the first buffer circuit is configured to amplify the detection signal subjected to the differential amplification at a specified ratio, and output the amplified detection signal;

the second buffer circuit has a receiving terminal connected to the reference signal input terminal and an output terminal coupled to the receiving terminal of the phase detecting circuit, and the second buffer circuit is configured to amplify the reference signal at the specified ratio, and output the amplified reference signal;

the phase detecting circuit has an output terminal coupled to a receiving terminal of the filter circuit, and the phase detecting circuit is configured to calculate the amplitude ratio or the phase difference, convert the amplitude ratio or the phase difference into a phase difference voltage signal to be outputted; and the filter circuit has an output terminal coupled to a receiving terminal of the compensation module, and the filter circuit is configured to filter the phase difference voltage signal to obtain the first phase difference voltage signal to be outputted.

12. The magnetic induction imaging device according to claim 11, the phase detecting circuit is an analog phase detecting chip.

13. The magnetic induction imaging device according to claim 11, wherein the filter circuit is an active low pass filter.

14. The magnetic induction imaging device according to claim 10, wherein:

the compensation voltage adjustment module comprises a temperature acquisition module, a micro control unit, a programmable resistor network, and a voltage divider network;

the temperature acquisition module is configured to collect the ambient temperature parameter;

the micro control unit is coupled to the temperature acquisition module, the voltage input terminal, and the programmable resistor network, respectively, and the micro control unit is configured to receive the ambient temperature parameter and the voltage value inputted from the voltage input terminal, and compare the ambient temperature parameter with a specified temperature threshold parameter, and then output a control signal and the voltage value according to a result of the comparison;

an output terminal of the programmable resistor network is coupled to the voltage divider network, and the programmable resistor network is configured to perform voltage division on the voltage value according to the control signal to obtain a first voltage value and output the first voltage value; and an output terminal of the voltage divider network is connected to the compensation module, and the voltage divider network is configured to perform secondary voltage division on the first voltage value to generate a second voltage value, and convert the second voltage value into a compensation voltage signal, and then output the compensation voltage signal.

15. The magnetic induction imaging device according to claim 10, wherein the compensation module comprises a voltage amplifier connected to the filter circuit and the voltage divider network, respectively, and the voltage amplifier is configured to amplify the first phase difference voltage signal and the second phase difference voltage signal at the same ratio.

16. A phase compensation method applied to a phase compensation circuit, the phase compensation circuit comprising:

providing a phase difference voltage detection module, a compensation voltage adjustment module, and a compensation module, wherein:

the phase difference voltage detection module is connected to a detection signal input terminal, a reference signal input terminal and a phase difference voltage output terminal, the phase difference voltage output terminal is coupled to the compensation module, and the phase difference voltage detection module is configured to process an inputted detection signal and an inputted reference signal, calculate a magnitude ratio of the processed detection signal and reference signal or a phase difference of the processed detection signal and reference signal, and then output a first phase difference voltage signal according to the amplitude ratio or the phase difference; and the compensation voltage adjustment module is connected to a voltage input terminal and a compensation voltage output terminal, the compensation voltage output terminal is coupled to the compensation module, and the compensation voltage adjustment module is configured to collect an ambient temperature parameter, determine a first compensation voltage corresponding to the ambient temperature parameter according to a corresponding relationship between a preset temperature parameter and a compensation voltage, perform voltage division on a voltage value inputted from the voltage input terminal according to the first compensation voltage, and output a compensation voltage signal; and the compensation module is configured to compensate for the first phase difference voltage signal according to the compensation voltage signal, and output a second phase difference voltage signal, inputting a detection signal to a detection signal input terminal, a reference signal to a reference signal input terminal, and a voltage value to a voltage input terminal, respectively;

determining a phase difference voltage signal based on an amplitude ratio of or a phase difference between the detection signal and the reference signal;

collecting an ambient temperature parameter;

determining a first compensation voltage corresponding to the ambient temperature parameter according to a correspondence relationship between a preset temperature parameter and a compensation voltage;

performing voltage division on the voltage value according to the first compensation voltage to output a compensation voltage signal; and performing phase compensation on the phase difference voltage signal according to the compensation voltage signal.

17. The phase compensation method according to claim 16, wherein:

the phase difference voltage detection module comprises a differential amplifier circuit, a first buffer circuit, a second buffer circuit, a phase detecting circuit, and a filter circuit;

the differential amplifier circuit has a terminal coupled to the detection signal input terminal and another terminal coupled to a receiving terminal of the first buffer circuit, and the differential amplifier circuit is configured to perform differential amplification on the detection signal, and output the detection signal on which the differential amplification is performed;

the first buffer circuit has an output terminal which is coupled to a receiving terminal of the phase detecting circuit, and the first buffer circuit is configured to amplify the detection signal subjected to the differential amplification at a specified ratio, and output the amplified detection signal;

the second buffer circuit has a receiving terminal connected to the reference signal input terminal and an output terminal coupled to the receiving terminal of the phase detecting circuit, and the second buffer circuit is configured to amplify the reference signal at the specified ratio, and output the amplified reference signal;

the phase detecting circuit has an output terminal coupled to a receiving terminal of the filter circuit, and the phase detecting circuit is configured to calculate the amplitude ratio or the phase difference, convert the amplitude ratio or the phase difference into a phase difference voltage signal to be outputted; and the filter circuit has an output terminal coupled to a receiving terminal of the compensation module, and the filter circuit is configured to filter the phase difference voltage signal to obtain the first phase difference voltage signal to be outputted.

18. The phase compensation method according to claim 17, wherein the phase detecting circuit is an analog phase detecting chip.

19. The phase compensation method according to claim 17, wherein the filter circuit is an active low pass filter.

20. The phase compensation method according to claim 16, wherein:

the compensation voltage adjustment module comprises a temperature acquisition module, a micro control unit, a programmable resistor network, and a voltage divider network;

the temperature acquisition module is configured to collect the ambient temperature parameter;

the micro control unit is coupled to the temperature acquisition module, the voltage input terminal, and the programmable resistor network, respectively, and the micro control unit is configured to receive the ambient temperature parameter and the voltage value inputted from the voltage input terminal, and compare the ambient temperature parameter with a specified temperature threshold parameter, and then output a control signal and the voltage value according to a result of the comparison;

an output terminal of the programmable resistor network is coupled to the voltage divider network, and the programmable resistor network is configured to perform voltage division on the voltage value according to the control signal to obtain a first voltage value, and output the first voltage value; and an output terminal of the voltage divider network is connected to the compensation module, and the voltage divider network is configured to perform secondary voltage division on the first voltage value to generate a second voltage value, and convert the second voltage value into a compensation voltage signal, and then output the compensation voltage signal.

\* \* \* \* \*